United States Patent [19]

Nara et al.

[11] 4,455,306

[45] Jun. 19, 1984

[54] METHOD FOR CONCENTRATING β-LACTAM ANTIBIOTIC SOLUTION

[75] Inventors: Kiyoshi Nara, Kyoto; Kazuyoshi Katamoto, Suita; Sadao Ohkido, Nakano; Isao Yamamoto, Chiba; Hiroshi Yanome, Matsudo, all of Japan

[73] Assignee: Takeda Chemical Industries, Ltd., Osaka, Japan

[21] Appl. No.: 333,182

[22] Filed: Dec. 21, 1981

[30] Foreign Application Priority Data

Dec. 24, 1980 [JP] Japan ................................ 55-184597

[51] Int. Cl.$^3$ ............................................ A61K 31/54
[52] U.S. Cl. ...................................... 424/246; 544/30; 544/16
[58] Field of Search .................... 544/30, 16; 424/246; 210/500.2, 651, 654

[56] References Cited

PUBLICATIONS

Matsuura et al., Physio Chem. Criteria for Reverse Osmosis . . . Membranes, J. Appl. Poly. Sci. 15:2905–2927.

Primary Examiner—Jerome D. Goldberg
Assistant Examiner—John Rollins
Attorney, Agent, or Firm—Wenderoth, Lind & Ponack

[57] ABSTRACT

The present invention relates to a method for concentrating a dilute aqueous solution of a β-lactam antibiotic which is readily susceptible to heat, by subjecting a dilute aqueous solution of a β-lactam antibiotic, said solution containing 2 to 20% (v/v) of a lower alcohol, to concentration by means of a permeable membrane made of poly(ether/amide) or polybenzimidazolone.

2 Claims, No Drawings

METHOD FOR CONCENTRATING β-LACTAM ANTIBIOTIC SOLUTION

The present invention relates to a method for concentrating a dilute aqueous solution of a β-lactam antibiotic which is readily susceptible to heat. Differently stated, the object of the present invention is to concentrate efficiently the said dilute aqueous solution by subjecting it to permeation with a permeable membrane in the presence of a lower alcohol, without bringing about decomposition of the β-lactam antibiotic.

As the means of purifying β-lactam antibiotics or their intermediates obtained by a fermentative process, frequent use has been made of chromatography on a variety of adsorbent materials, which β-lactam antibiotics are usually obtained in a form of a very dilute solution. The thus-obtained dilute solution is concentrated generally by employing an evaporator under heating thereby to evaporate water. However, most of the β-lactam antibiotics are unstable to heat and highly susceptible to thermal decomposition during the concentration, whereas the concentration at a relatively lower temperature requires an enormous quantity of energy source such as steam.

Recently, non-heating or low-temperature concentration with use of permeable membrane has come to be attempted in various processes in the fields of chemicals, food and pharmaceuticals, and it is the common technical knowledge to remove any solvent other than water before the concentration with the use of permeable membrane, whenever it coexists. Thus, the present inventors, in concentration of a dilute solution of a β-lactam antibiotic in aqueous methanol obtained by chromatography, first removed the methanol by evaporation at a relatively low temperature and then subjected the remaining aqueous solution to concentration by the use of a permeable membrane. This process, however, often gives poor concentration yields and brings about a greater extent of decomposition.

In view of these facts, the inventors further tried to concentrate directly with use of permeable membrane a dilute solution of a β-lactam antibiotic in aqueous methanol obtained by chromatography and, as a result, found that the concentration, unexpectedly, can be successfully performed and that not only decomposition of the β-lactam antibiotic is reduced but also its leak into the permeated liquid is lessened. The inventors, after having conducted extensive investigation on the basis of such findings, have completed the present invention.

On separation by permeation of ultradilute aqueous solutions of alcohols, the following reports, among others, have been made, i.e. 0.001 to 0.006 g mol/l, 0.002 to 0.1% (V/V) in the case of methanol, (hereinafter, solvents are all indicated in V/V%), Journal of Applied Polymer Science, vol. 15 (1971), pp. 2905 to 2927; 700 ppm=0.07% in the case of ethanol, R. L. Riley et al. at the Membrane Separation Technology Conference held at Clemson Univ. on Aug. 2 to 6, 1976, but these two reports disclosed that alcohols do not permeate through the membrane. In attempting concentration in the presence of a solvent by means of permeable membrane, the present inventors investigated effects of methanol on the membrane with a dilute solution of deacetylcephalosporin C (DCPC) in methanol (DCPC: about 5,000 μg/ml, 15% of methanol) used as a representative example, while selecting for permeable membranes Cellulose Acetate Membrane (Daicel Ltd.), B-9 (E. I. Du Pont de Nemours & Co.) and PA-300 (Universal Oil Products Co.) as the membranes made of cellulose acetate, polyamide and poly(ether/amide), respectively. As a result, it was confirmed that although the cellulose acetate flat membrane and polyamide B-9 membrane were torn after usage for several days, the poly(ether/amide) PA-300 membrane showed excellent methanol resistance sufficient to be used for a prolonged period of time. Furthermore, the present inventors reached the findings advantageous to the industrial application that methanol is not prevented from permeating and is allowed to move freely into the permeated liquid and that leak of DCPC into the permeated liquid is reduced to a greater extent in the presence of methanol than in an aqueous solution. Thus, the present inventors obtained a promising prospect of the concentration by means of permeable membrane in the presence of a solvent and conducted further detailed examination of the kind and concentration of solvents, β-lactam antibiotics and other applicable conditions to complete the present invention.

Thus, the present invention covers a method for concentrating β-lactam antibiotic solution, which comprises concentrating an aqueous dilute solution of a β-lactam antibiotic, said solution containing 2 to 20% of a lower alcohol, by means of permeable membrane made of poly(ether/amide) or polybenzimidazolone.

As the lower alcohol contained in the starting aqueous solution in the present invention, methanol, ethanol, propanol, butanol, etc. are of first choice. Referring to the concentration of the lower alcohol, 2 to 20% is the most easy-to-handle concentration, whereby the concentration of not more than 2% leads to higher decomposition of the solute and that of not less than 20% causes many difficulties in concentration. Although methanol can permeate freely through permeable membranes, the permeation ratio lowers with the increase of the alcohol's molecular weight as is the case with propanol, butanol, etc. This causes a gradual increase of alcohol concentration other than methanol in the concentrated liquid as concentration proceeds, even if their concentration in the starting solution is low, and it is therefore preferred to adjust their initial concentration to such an appropriate extent as may not bring about difficulty.

The solute to be concentrated in the present method may be theoretically of any kind, but one of the typical and effective examples to which the present method is applicable is a thermally unstable β-lactam antibiotic to be obtained by fermentation, especially that in a dilute eluate resulting from purification by means of chromatography.

Specifically, for example, cephalosporin C (CPC), deacetylcephalosporin C (DCPC), deacetoxycephalosporin C (DACPC) and their 7-position deacylated compounds (particularly, in the case of deacylation effected by the microbial process) are suitable materials for the application of this method. The range of concentration of these solutes is not particularly limited, and is normally 0.01 to 5% (W/V), preferably 0.1 to 1% (W/V).

The permeable membrane usable in the method of the present invention is required to be lower-alcohol resistant, because it is to be used in the presence of a highly concentrated lower alcohol, and there may be employed, for example, those made of poly(ether/amide) (PA-300, PEC-1000 manufactured by Toray Industries, Inc., etc.) and polybenzimidazolone (PBIL manufactured by Teijin Limited). The poly(ether/amide) membrane may be prepared, for example, by an interfacial polymerization technique. Briefly stated, the membrane is prepared by depositing a thin layer of an aqueous solution of an epichlorohydrin-ethylene diamine condensate on the finely porous surface of a polysulfone support membrane and subsequently contacting the poly(ether/amine) layer with a water immiscible solution of isophthalyldichloride. A thin semipermeable film, a crosslinked poly(ether/amide) copolymer, is formed at the interface. Subsequently, the membrane is dried at an elevated temperature.

The concentration of the present method may be carried out at room temperature, e.g. 10°–35° C., preferably 25°–30° C. Other conditions for the concentration by means of permeable membranes can be appropriately selected according to normally employed conditions. The concentrated liquid obtained by the method of the present invention, after repeating the method of the present invention as necessary, may be subjected to a conventional purification method to isolate the solute.

EXAMPLE 1

In 8,000 l of 10% aqueous methanol is dissolved in 50 kg of crystalline DCPC sodium salt (water content 14.81%). The solution 8,000 l (25° C.) is fed into a concentrator utilizing permeable membranes [poly(ether/amide) membrane, spiral wound type element of 6 inch diameter by 36 inch length, marketed by Universal Oil Products Co., under the tradename 1501PA], at a circulating flow rate of 5,000 l/hr and under a pressure of 40 kg/cm$^2$G. The concentration is conducted for 24 hours continuously to obtain 800 l of the concentrate and 7,200 l of the permeate. The contents of DCPC in the concentrate and the permeate are 49.2 mg/ml and 0.078 mg/ml, respectively.

The same experiment as above is conducted ten times in all. The following table shows DCPC content (%) in the concentrate. DCPC content (%) leaked into the permeate and the amount (%) of DCPC decomposed during the concentration.

| Experiment number | DCPC in the concentrate % | DCPC leaked into the permeate % | DCPC decomposed % |
| --- | --- | --- | --- |
| 1 | 97.8 | 1.4 | 0.8 |
| 2 | 97.4 | 1.5 | 1.1 |
| 3 | 98.1 | 1.3 | 0.6 |
| 4 | 99.0 | 1.0 | 0 |
| 5 | 98.3 | 0.7 | 1.0 |
| 6 | 97.2 | 1.9 | 0.9 |
| 7 | 97.0 | 1.7 | 1.3 |
| 8 | 96.4 | 2.1 | 1.5 |
| 9 | 98.2 | 1.0 | 0.8 |
| 10 | 97.6 | 0.9 | 1.5 |

For the purpose of comparison, the experiment of concentration by use of permeable membrane is repeatedly conducted under the same conditions with a solution of 50 kg of crystals of DCPC sodium salt in 8000 l of pure water, and the following results are obtained.

| Experiment number | DCPC in the concentrate % | DCPC leaked into the permeate % | DCPC decomposed % |
| --- | --- | --- | --- |
| 1 | 82.9 | 2.4 | 14.7 |
| 2 | 69.7 | 3.1 | 27.2 |
| 3 | 88.3 | 3.6 | 8.1 |
| 4 | 83.8 | 2.9 | 13.3 |
| 5 | 86.7 | 3.3 | 10.0 |
| 6 | 93.1 | 2.5 | 4.4 |

EXAMPLE 2

A 1,000 ml portion of the culture medium containing 3.0% of sucrose, 1.5% of meat extract, 0.5% of corn steep liquor and 0.15% of CaCO$_3$ is poured in equal volumes into two 2-l Sakaguchi flasks and sterilized. The culture media are inoculated with *Cephalosporium acremonium* K-121 (Receipt Number of a Written Application for Deposit and Maintenance of Microorganism at Fermentation Research Institute: No. 2285), and the culture is carried out on a reciprocating shaker at 28° C. for 3 days. On the other hand, 100 l of the culture medium containing 6% of sucrose, 5% of glucose, 3% of peanut cake, 3% of soybean flour, 1.0% of DL-methionine and 0.15% of CaCO$_3$ is charged into a 200 l-capacity fermentation tank made of stainless steel, and is sterilized and cooled by a conventional procedure. The culture medium is inoculated under sterile conditions with the culture broth obtained above, and cultured with forced aeration at 28° C. After fermentation for 190 hours, the culture broth is subjected to filtration to remove solids. The mixture (192 l) of resultant filtrate and washings is assayed to find CPC content as 4,900 μg/ml. The mixture (192 l) is in the first place allowed to pass through a column of Amberlite IRA-402 (acetate type, manufactured by Rohm & Haas Co.) to allow CPC to be adsorbed. The adsorbed CPC is eluted with an ammonium acetate buffer (pH 5.0, 0.2 M), whereby the CPC fraction is obtained. The eluate fraction is allowed to pass through a column of activated carbon (50 l) to allow CPC to be adsorbed.

After the column is washed with water completely, elution is carried out with 10% aqueous ethanol, containing 0.01 N NaOH to afford 198 l of the CPC fraction containing (432 g of CPC).

198 l of the 10% aqueous ethanol solution containing 432 g of CPC, after being adjusted to pH 7.0, is fed to a concentrating equipment utilizing permeable membrane (PA 300 membrane produced by Universal Oil Products Co., spiral wound type with membrane surface area of about 0.3 m$^2$), at a circulating flow rate of 450 l/hr and under a pressure of 40 kg/cm$^2$G, and the concentration is carried out for about 20 hours at 30° C., thereby yielding 5.8 l of the concentrate and 192 l of the permeate. Determination of the content of CPC gives the value of 98.4% in the concentrate, leaked CPC into the permeate 0.9% and 0.7% untraceable CPC (assumed to have decomposed).

EXAMPLE 3

A 1,000 ml portion of a seed culture medium containing 3.0% of sucrose, 1.5% of meat extract, 0.5% of corn steep liquor and 0.15% of CaCO$_3$ is poured into two 2 l-capacity Sakaguchi flasks and sterilized. These culture media are respectively inoculated with *Cephalosporium acremonium* C-132 (ATCC-20371) and cultured on a reciprocating shaker at 28° C. for 3 days. On the other hand, a 200 l fermentation tank made of stainless steel is charged with 100 l of a culture medium containing 3.0% of sucrose, 3.2% of raw soybean flour, 0.5% of DL-methionine and 0.16% of CaCO₃, which is sterilized and cooled beforehand by a conventional procedure. The culture medium is inoculated with the seed culture broth as described above under sterile conditions and cultured with forced aeration at 28° C. After fermentation for 132 hours, the culture broth is subjected to filtration, and the mixture of the resultant filtrate and washings (168 l in total) is assayed to find the content of DCPC as 850 μg/ml.

The mixture (84 l) is allowed to pass through a column of Amberlite IRA-900 (acetate type, manufactured by Rohm & Haas Co.) to allow DCPC to be adsorbed thereon. The adsorbed DCPC is eluted with an ammonium acetate buffer (pH 5.0, 0.2 M), and the DCPC fractions are pooled. The pooled DCPC fraction is allowed to pass through a column of activated carbon (15 l) to allow DCPC to be adsorbed thereon. After the column is washed with water completely, elution is carried out with 15% aqueous methanol, whereby 30 l of the DCPC fraction (containing 2,620 μg/ml of DCPC) is obtained.

The above procedure is repeatedly carried out until 200 l (containing 500 g of DCPC) of the eluted solution containing 15% methanol is obtained and the solution is concentrated by a concentrating equipment utilizing the same membrane under the same conditions as in Example 2. The concentration is carried out for about 20 hours at 25° C., thus yielding 7 l of the concentrate and 193 l of the permeate. Determination of the content of DCPC reveals the content of DCPC in the concentrate as 97.9%, DCPC leaked into the permeate as 1.3% and DCPC which cannot be traced as 0.8%.

EXAMPLE 4

A 500 g quantity of crystals of DCPC sodium salt is dissolved in 200 l each of 2% aqueous ethanol, 2% aqueous propanol and 2% aqueous butanol, followed by conducting concentration by means of permeable membranes with use of the same equipment, and under the same conditions, as in Example 2. The following results are obtained.

|  | DCPC in the concentrate | DCPC leaked | DCPC decomposed |
| --- | --- | --- | --- |
| For 2% aqueous ethanol | 97.1% | 2% | 0.9% |
| For 2% aqueous propanol | 97.2% | 1.3% | 1.5% |
| For 2% aqueous butanol | 97.1% | 1.9% | 1.0% |

REFERENCE EXPERIMENT 1

A 15% (V/V) aqueous methanol solution containing 0.7% of DCPC is concentrated in a concentrating equipment utilizing permeable membrane (cellulose acetate membrane produced by Daicel Co., flat membrane of about 15 cmφ used) under pressure at 30 kg/cm²G at 25° C., whereby the rate of permeation decreases sharply after about 30 hours elapsed, thus making operation of the equipment impossible.

REFERENCE EXPERIMENT 2

A 200 l portion of 15% (V/V) aqueous methanol solution containing 0.6% of DCPC is fed into a concentrating equipment utilizing permeable membrane (polyamide based hollow fiber, type B-9, produced by E. I. Du Pont de Nemours Co., element of 10 cm diameter and 90 cm length used) at 25° C. and at a circulating flow rate of 250 l/hr under pressure at 28 kg/cm²G, whereby there are obtained 19 l of the concentrate and 181 l of the permeate after 65 minutes. Determination of the contents of DCPC in these liquids reveals DCPC in the concentrate: 87%, and DCPC leaked into the permeate: 11.2%. When the same experiment is conducted three times repeatedly, the hollow fiber is torn and becomes impossible to use.

What we claim is:

1. A method for concentrating β-lactam antibiotic solution, which comprises subjecting a dilute aqueous solution of a β-lactam antibiotic selected from the group consisting of cephalosporin C, deacetylcephalosporin C, deacetoxycephalosporin C and their 7-position deacylated compounds, said solution containing 0.01 to 5% (w/v) of the β-lactam antibiotic and 2 to 20% (v/v) of a lower alcohol selected from the group consisting of methanol, ethanol, propanol and butanol, to concentration at a temperature of 10° to 35° C. by means of a permeable poly-(ether/amide) membrane prepared by depositing a thin layer of an aqueous solution of an epichlorohydrin-ethylene diamine condensate on the finely porous surface of a polysulfone support membrane and subsequently contacting the said poly-(ether-/amine) layer with a water immiscible solution of isophthalyldichloride.

2. A method as claimed in claim 1, wherein the lower alcohol is methanol.

* * * * *